United States Patent

Worthington et al.

[11] Patent Number: 5,935,999
[45] Date of Patent: Aug. 10, 1999

[54] ARALKYOXY ALKOXIMINO DERIVATIVES AND THEIR USE AS FUNGICIDES

[75] Inventors: Paul Anthony Worthington, Maidenhead; Ian Henry Aspinall, Bracknell, both of United Kingdom

[73] Assignee: Zeneca Limited, London, United Kingdom

[21] Appl. No.: 08/448,615

[22] PCT Filed: Dec. 2, 1993

[86] PCT No.: PCT/GB93/02478

§ 371 Date: Jul. 31, 1995

§ 102(e) Date: Jul. 31, 1995

[87] PCT Pub. No.: WO94/14761

PCT Pub. Date: Jul. 7, 1994

[30] Foreign Application Priority Data

Dec. 23, 1992 [GB] United Kingdom ............... 9226865

[51] Int. Cl.$^6$ ................................................. A61K 31/15
[52] U.S. Cl. .......................... 514/640; 514/538; 560/35
[58] Field of Search ......................... 514/619, 621, 514/622, 644, 538, 539, 640; 546/332; 560/564, 163, 164, 166

[56] References Cited

U.S. PATENT DOCUMENTS

| | | | |
|---|---|---|---|
| 5,055,471 | 10/1991 | de Fraine et al. | 514/255 |
| 5,221,691 | 6/1993 | Clough et al. | 514/619 |
| 5,238,956 | 8/1993 | Clough et al. | 514/506 |

FOREIGN PATENT DOCUMENTS

| | | |
|---|---|---|
| 2005345 | 6/1990 | Canada . |
| 0 370 629 | 5/1990 | European Pat. Off. . |
| 0 426 460 | 5/1991 | European Pat. Off. . |
| 4-182461 | 11/1990 | Japan . |
| 92/18487 | 12/1989 | WIPO . |
| 90/07493 | 7/1990 | WIPO . |
| 92/18494 | 10/1992 | WIPO . |
| 94/08968 | 4/1994 | WIPO . |

Primary Examiner—Jose' G. Dees
Assistant Examiner—Barbara Badio

[57] ABSTRACT

A compound of formula (I):

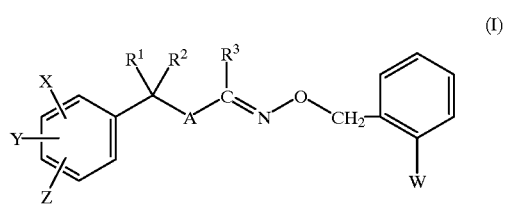

wherein A is oxygen, W is $CH_3O.CH=CCO_2CH_3$ and $R^1$, $R^2$, $R^3$, X, Y and Z are as defined in the specification. The compounds are useful as plant fungicides and insecticides.

11 Claims, No Drawings

ARALKYOXY ALKOXIMINO DERIVATIVES AND THEIR USE AS FUNGICIDES

This application is a 371 of PCT/GB93/02478 filed Dec. 2, 1993.

The present invention relates to oxime derivatives that are useful as fungicides, to a process for preparing them, to compositions containing them and to methods of using them to combat fungi, especially fungal infections of plants.

According to the present invention there is provided a compound having the general formula (I), wherein $R^1$ and $R^2$ are independently hydrogen, $C_{1-4}$ alkyl, $C_{1-4}$ haloalkyl, $C_{2-4}$ alkenyl, $C_{2-4}$ alkynyl, $C_{3-6}$ cycloalkyl, aryl or aryl($C_{1-4}$)alkyl; $R^3$ is hydrogen, $C_{1-4}$ alkyl, $C_{1-4}$ haloalkyl or $C_{3-6}$ cycloalkyl; A is oxygen or sulphur; W is $CH_3O.CH=CCO_2CH_3$, $CH_3O.N=CCONR^4R^5$, $CH_3O.CH=CCONR^4R^5$ or $CH_3O.N=CCO_2CH_3$ and stereoisomers thereof; X, Y and Z are independently hydrogen, halogen, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted methylenedioxy (especially optionally substituted with fluorine or $C_{1-4}$ alkyl), optionally substituted aryl (especially optionally substituted phenyl), optionally substituted heteroaryl (especially optionally substituted pyridyl or pyrimidinyl), optionally substituted heterocyclyl (especially optionally substituted pyrrolidine), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl ($C_{1-4}$) alkyl (especially optionally substituted pyridyl- or pyrimidinyl($C_{1-4}$)alkyl), optionally substituted aryl($C_{2-4}$) alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$) alkoxy (especially optionally substituted benzyloxy), optionally substituted heteroaryl($C_{1-4}$ )alkoxy (especially optionally substituted pyridyl- or pyrimidinyl($C_{1-4}$)alkoxy), optionally substituted aryloxy($C_{1-4}$)alkyl (especially phenoxymethyl), optionally substituted heteroaryloxy($C_{1-4}$) alkyl (especially optionally substituted pyridyloxy- or pyrimidinyloxy($C_{1-4}$)alkyl), acyloxy (including $C_{1-4}$ alkanoyloxy (especially acetyloxy) and benzoyloxy), cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$ )alkyl, phenyl or benzyl, the phenyl and benzyl groups being optionally substituted with halogen, $C_{1-4}$ alkyl or $C_{1-4}$ alkoxy; when R' and R" are in CONR'RN" they can together form a 5- or 6-membered heterocyclic ring (for example a pyrrole, imidazole, pyrrolidine, piperidine or morpholine ring); or two substituents, when they are in adjacent positions on the aryl or heteroaryl ring can join to form a fused alphatic ring (especially to form a fused 6-membered carbon aliphatic ring); and $R^4$ and $R^5$ are independently hydrogen or $C_{1-4}$ alkyl.

Because the double bond of the propenoate, oxyiminoacetamide or oxyiminoacetate group is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomers are the more fungicidally active and form a preferred embodiment of the invention.

Optionally substituted methylenedioxy includes —OCH$_2$O—, —OCHFO—, —OCF$_2$O—, —OCH(CH$_3$)O— and —OC(CH$_3$)$_2$O—.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R" in which R' and R" have the meanings given above.

It is preferred that $R^4$ is hydrogen and $R^5$ is methyl.

Aryl is preferably phenyl.

Heteroaryl includes 5- and 6-membered aromatic rings containing one or more heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl, furyl, thienyl, pyrrolyl, pyrazolyl, imidazolyl, triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothiophenyl and benzimidazolinyl.

Alkyl moieties and the alkyl moiety of alkoxy and haloalkyl preferably contain, unless otherwise stated, from 1 to 6, more preferably from 1 to 4, carbon atoms. They can be in the form of straight or branched chains, for example methyl, ethyl, n- or iso- propyl, or n-, sec-, iso- or tert-butyl.

Alkenyl and alkynyl moieties preferably contain, unless otherwise stated, from 2 to 6, more preferably from 2 to 4, carbon atoms. They can be in the form of straight or branched chains, and the alkenyl moieties, where appropriate, may have either the (E)- or (Z)-configuration. Examples are vinyl, allyl and propargyl.

Halogen is typically fluorine, chlorine or bromine.

In one aspect the present invention provides a compound of formula (I) wherein W is $CH_3O.CH=CCO_2CH_3$ and A, X, Y, Z, $R^1$, $R^2$ and $R^3$ are as defined above.

It is preferred that A is oxygen.

It is preferred that $R^3$ is hydrogen or $C_{1-4}$ alkyl. $R^3$ is especially methyl.

In a further aspect the present invention provides a compound of formula (I) wherein $R^1$ and $R^2$ are, independently, hydrogen or $C_{1-4}$ alkyl (especially methyl). It is preferred that $R^1$ and $R^2$ are both hydrogen.

In another aspect the present invention provides a compound of formula (I) wherein A is oxygen; W is $CH_3O.CH=CCO_2CH_3$; $R^1$ and $R^2$ are, independently hydrogen or $C_{1-4}$ alkyl (preferably both hydrogen); $R^3$ is methyl; and X, Y and Z are as previously defined.

In a further aspect the present invention provides a compound of formula (I) wherein X, Y and Z are, independently, hydrogen, halogen, hydroxy, mercapto, $C_{1-4}$ alkyl, $C_{2-4}$ alkenyl, $C_{2-4}$ alkynyl, halo($C_{1-4}$)alkyl, $C_{1-4}$ alkoxy, $C_{2-4}$ alkenyloxy, $C_{2-4}$ alkynyloxy, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, acyloxy, cyano, thiocyanato, nitro, —NR'R", —NHCOR', —CONR'R", —COOR' or —COR', wherein R' and R" are, independently, hydrogen, $C_{1-4}$ alkyl or $C_{3-6}$ cycloalkyl.

In a still further aspect the present invention provides a compound of formula (I) wherein A is oxygen; W is $CH_3O.CH=CCO_2CH_3$; $R^1$ and $R^2$ are both hydrogen; $R^3$ is methyl; and X, Y and Z are independently, hydrogen, halogen, hydroxy, mercapto, $C_{1-4}$ alkyl, $C_{2-4}$ alkenyl, $C_{2-4}$ alkynyl, halo($C_{1-4}$)alkyl, $C_{1-4}$ alkoxy, $C_{2-4}$ alkenyloxy, $C_{2-4}$ alkynyloxy, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, acyloxy, cyano, thiocyanato, nitro, —NR'R", —NHCOR', —CONR'R", —COOR' or —COR', wherein R' and R" are, independently, hydrogen, $C_{1-4}$ alkyl or $C_{3-6}$ cycloalkyl.

In another aspect the present invention provides a compound of formula (I) wherein X, Y and Z are, independently, hydrogen, halogen (especially chlorine or fluorine), $C_{1-4}$ alkyl (especially methyl, ethyl, n-propyl or iso-propyl), cyano, $C_{1-4}$ alkoxy (especially methoxy, ethoxy, n-propyloxy or iso-propyloxy), halo($C_{1-4}$)alkyl (especially $CF_3$), halo($C_{1-4}$)alkoxy (especially $OCF_3$) or nitro.

In another apspect the present invention provides a compound of formula (I) wherein $R^1$ is hydrogen or $C_{1-4}$ alkyl (especially methyl); $R^2$ is hydrogen; $R^3$ is $C_{1-4}$ alkyl (especially methyl); A is oxygen; W is $CH_3O.CH=CCO_2CH_3$, $CH_3O.N=CCO_2CH_3$, $CH_3O.N=CCONHR^5$ or $CH_3O.CH=CCONHR^5$ (wherein $R^5$ is $C_{1-4}$ alkyl (especially methyl)); and Y and Z are both hydrogen and X is hydrogen, halogen (especially chlorine), $C_{1-4}$ alkyl (especially methyl), cyano or $C_{1-4}$ alkoxy (especially methoxy).

The present invention is illustrated by compounds of formula (I) which are listed in Tables 1 to 4. Compounds in Table 1 are of general formula (I) wherein W is $CH_3O.CH=CCO_2CH_3$ and A is oxygen.

TABLE 1

| Compound No | X | Y | Z | $R^1$ | $R^2$ | $R^3$ |
|---|---|---|---|---|---|---|
| 1 | H | H | H | H | H | $CH_3$ |
| 2 | 2-Cl | H | H | H | H | $CH_3$ |
| 3 | 2-$CH_3$ | H | H | H | H | $CH_3$ |
| 4 | 2-CN | H | H | H | H | $CH_3$ |
| 5 | H | H | H | H | H | H |
| 6 | H | H | H | $CH_3$ | H | $CH_3$ |
| 7 | 3-$CH_3$ | H | H | H | H | $CH_3$ |
| 8 | 4-$CH_3$ | H | H | H | H | $CH_3$ |
| 9 | 2-$OCH_3$ | H | H | H | H | $CH_3$ |
| 10 | 3-$CF_3$ | H | H | H | H | CH |
| 11 | 3-Cl | H | H | H | H | $CH_3$ |
| 12 | 4-Cl | H | H | H | H | $CH_3$ |
| 13 | 3-CN | H | H | H | H | $CH_3$ |
| 14 | 4-CN | H | H | H | H | $CH_3$ |
| 15 | 3-$OCH_3$ | H | H | H | H | $CH_3$ |
| 16 | 4-$OCH_3$ | H | H | H | H | $CH_3$ |
| 17 | 2-F | H | H | H | H | $CH_3$ |
| 18 | 3-F | H | H | H | H | $CH_3$ |
| 19 | 4-F | H | H | H | H | $CH_3$ |
| 20 | 2-Br | H | H | H | H | $CH_3$ |
| 21 | 3-Br | H | H | H | H | $CH_3$ |
| 22 | 4-Br | H | H | H | H | $CH_3$ |
| 23 | 2-I | H | H | H | H | $CH_3$ |
| 24 | 3-I | H | H | H | H | $CH_3$ |
| 25 | 4-I | H | H | H | H | $CH_3$ |
| 26 | 2-$C_2H_5$ | H | H | H | H | $CH_3$ |

TABLE 1-continued

| Compound No | X | Y | Z | $R^1$ | $R^2$ | $R^3$ |
|---|---|---|---|---|---|---|
| 27 | 3-$C_2H_5$ | H | H | H | H | $CH_3$ |
| 28 | 4-$C_2H_5$ | H | H | H | H | $CH_3$ |
| 29 | 2-$C_2H_5O$ | H | H | H | H | $CH_3$ |
| 30 | 3-$C_2H_5O$ | H | H | H | H | $CH_3$ |
| 31 | 4-$C_2H_5O$ | H | H | H | H | $CH_3$ |
| 32 | 2-$(CH_3)_2CH$ | H | H | H | H | $CH_3$ |
| 33 | 3-$(CH_3)_2CH$ | H | H | H | H | $CH_3$ |
| 34 | 4-$(CH_3)_2CH$ | H | H | H | H | $CH_3$ |
| 35 | 2-$(CH_3)_2CHO$ | H | H | H | H | $CH_3$ |
| 36 | 3-$(CH_3)_2CHO$ | H | H | H | H | CH |
| 37 | 4-$(CH_3)_2CHO$ | H | H | H | H | $CH_3$ |
| 38 | 2-$CF_3$ | H | H | H | H | $CH_3$ |
| 39 | 3-$CF_3$ | H | H | CH | CH | $CH_3$ |
| 40 | 4-$CF_3$ | H | H | H | H | $CH_3$ |
| 41 | 2-$CF_3O$ | H | H | H | H | $CH_3$ |
| 42 | 3-$CF_3O$ | H | H | H | H | $CH_3$ |
| 43 | 4-$CF_3O$ | H | H | H | H | $CH_3$ |
| 44 | 2-$CH_3(CH_2)_2$ | H | H | H | H | $CH_3$ |
| 45 | 3-$CH_3(CH_2)_2$ | H | H | H | H | $CH_3$ |
| 46 | 4-$CH_3(CH_2)_2$ | H | H | H | H | $CH_3$ |
| 47 | 2-$CH_3(CH_2)_2O$ | H | H | H | H | $CH_3$ |
| 48 | 3-$CH_3(CH_2)_2O$ | H | H | H | H | $CH_3$ |
| 49 | 4-$CH_3(CH_2)_2O$ | H | H | H | H | $CH_3$ |
| 50 | 2-Cl | 3-Cl | H | H | H | $CH_3$ |
| 51 | 2-Cl | 4-Cl | H | H | H | $CH_3$ |
| 52 | 2-Cl | 5-Cl | H | H | H | $CH_3$ |
| 53 | 2-Cl | 6-Cl | H | H | H | $CH_3$ |
| 54 | 2-F | 3-F | H | H | H | $CH_3$ |
| 55 | 2-F | 4-F | H | H | H | $CH_3$ |
| 56 | 2-F | 5-F | H | H | H | $CH_3$ |
| 57 | 2-F | 6-F | H | H | H | $CH_3$ |
| 58 | 3-Cl | 4-Cl | H | H | H | $CH_3$ |
| 59 | 3-F | 4-F | H | H | H | $CH_3$ |
| 60 | 3-Cl | 5-Cl | H | H | H | $CH_3$ |
| 61 | 3-F | 5-F | H | H | H | $CH_3$ |
| 62 | 2-Cl | 3-F | H | H | H | $CH_3$ |
| 63 | 2-Cl | 4-F | H | H | H | $CH_3$ |
| 64 | 2-F | 3-Cl | H | H | H | $CH_3$ |
| 65 | 2-F | 4-Cl | H | H | H | $CH_3$ |
| 66 | 3-F | 4-Cl | H | H | H | $CH_3$ |
| 67 | 3-Cl | 4-F | H | H | H | $CH_3$ |
| 68 | 2-F | H | H | H | $CH_3$ | $CH_3$ |
| 69 | 3-F | H | H | H | $CH_3$ | $CH_3$ |
| 70 | 4-F | H | H | H | $CH_3$ | $CH_3$ |
| 71 | 2-Cl | H | H | H | $CH_3$ | $CH_3$ |
| 72 | 3-Cl | H | H | H | $CH_3$ | $CH_3$ |
| 73 | 4-Cl | H | H | H | $CH_3$ | $CH_3$ |
| 74 | 2-$CF_3$ | H | H | H | $CH_3$ | $CH_3$ |
| 75 | 3-$CF_3$ | H | H | H | $CH_3$ | $CH_3$ |
| 76 | 4-$CF_3$ | H | H | H | $CH_3$ | $CH_3$ |
| 77 | 2-$OCH_3$ | H | H | H | $CH_3$ | $CH_3$ |
| 78 | 3-$OCH_3$ | H | H | H | $CH_3$ | $CH_3$ |
| 79 | 4-$OCH_3$ | H | H | H | $CH_3$ | $CH_3$ |
| 80 | 2-$CH_3$ | H | H | H | $CH_3$ | $CH_3$ |
| 81 | 3-$CH_3$ | H | H | H | $CH_3$ | $CH_3$ |
| 82 | 4-$CH_3$ | H | H | H | $CH_3$ | $CH_3$ |
| 83 | 2-CN | H | H | H | $CH_3$ | $CH_3$ |
| 84 | 3-CN | H | H | H | $CH_3$ | $CH_3$ |
| 85 | 4-CN | H | H | H | $CH_3$ | $CH_3$ |
| 86 | 2-$CF_3O$ | H | H | H | $CH_3$ | $CH_3$ |
| 87 | 3-$CF_3O$ | H | H | H | $CH_3$ | $CH_3$ |
| 88 | 4-$CF_3O$ | H | H | H | $CH_3$ | $CH_3$ |
| 89 | 2-$NO_2$ | H | H | H | H | $CH_3$ |
| 90 | 3-$NO_2$ | H | H | H | H | $CH_3$ |
| 91 | 4-$NO_2$ | H | H | H | H | $CH_3$ |
| 92 | 2-F | 3-F | 4-F | H | H | $CH_3$ |
| 93 | 3-F | 4-F | 5-F | H | H | $CH_3$ |
| 94 | 2-$CH_3$ | 4-Cl | H | H | H | $CH_3$ |
| 95 | 2-$CH_3$ | 4-F | H | H | H | $CH_3$ |
| 96 | 3-$CH_3$ | 4-Cl | H | H | H | $CH_3$ |
| 97 | 3-$CH_3$ | 4-F | H | H | H | $CH_3$ |
| 98 | 2-Cl | 3-Cl | 4-Cl | H | H | $CH_3$ |
| 99 | 3-Cl | 4-Cl | 5-Cl | H | H | $CH_3$ |
| 100 | H | H | H | $CH_3$ | $CH_3$ | $CH_3$ |
| 101 | 3-$OCH_3$ | 4-$OCH_3$ | H | H | H | $CH_3$ |

TABLE 2

Table 2 comprises 101 compounds of general formula (I) wherein W is $CH_3O.CH=CCONHCH_3$, A is oxygen and X, Y, Z, $R^1$, $R^2$ and $R^3$ are as listed in Table 1.

TABLE 3

Table 3 comprises 101 compounds of general formula (I) wherein W is $CH_3O.N=CCO_2CH_3$, A is oxygen and X, Y, Z, $R^1$, $R^2$ and $R^3$ are as listed in Table 1.

TABLE 4

Table 4 comprises 101 compounds of general formula (I) wherein W is $CH_3O.N=CCONHCH_3$, A is oxygen and X, Y, Z, $R^1$, $R^2$ and $R^3$ are as listed in Table 1.

TABLE 5

Table 5 comprises 101 compounds of general formula (I) wheerein W is $CH_3O.CH=CCO_2CH_3$, A is sulphur and X, Y, Z, $R^1$, $R^2$ and $R^3$ are as listed in Table 1.

TABLE 6

Table 6 comprises 101 compounds of general formula (I) wherein W is $CH_3O.CH=CCONHCH_3$, A is sulphur and X, Y, Z, $R^1$, $R^2$ and $R^3$ are as listed in Table 1.

TABLE 7

Table 7 comprises 101 compounds of general formula (I) wherein $CH_3O.N=CCO_2CH_3$, A is sulphur and X, Y, Z, $R^1$, $R^2$ and $R^3$ are as listed in Table 1.

TABLE 8

Table 8 comprises 101 compounds of general formula (I) wherein W is $CH_3O.N=CCONHCH_3$, A is sulphur and X, Y, Z, $R^1$, $R^2$ and $R^3$ are as listed in Table 1.

TABLE I

Table I gives melting points and proton NMR data obtained at 270 MHz for certain compounds described in Tables 1 to 4. Chemical shifts are measured at 20° C. in ppm from tetramethylsilane and deuterochloroform was used as solvent, unless otherwise stated. The following abbreviations are used:

s=singlet
m=multiplet
d=doublet
br=broad
t=triplet
ppm=parts per million

| Compound No. (Table) | Proton NMR Data (δ) |
|---|---|
| 1(1) | 1.98(3H, s); 3.68(3H, s); 3.80(3H, s); 4.89(2H, s); 4.97(2H, s); 7.12–7.18(1H, m); 7.25–7.37(7H, m); 7.45–7.51(1H, m); 7.58(1H, s)ppm. |
| 4(1) | 2.00(3H, s); 3.69(3H, s); 3.82(3H, s); 4.88(2H, s); 5.17(2H, s); 7.12–7.18(1H, m); 7.26–7.33(2H, m); 7.36–7.59(4H, m); 7.59(1H, s); 7.66(1H, d)ppm. |
| 7(1) | 1.91(3H, s); 2.18(3H, s); 3.67(3H, s); 3.79(3H, s); 4.93(2H, s); 5.14(2H, s); 7.08–7.38(7H, m); 7.48–7.58(1H, m); 7.58(1H, s)ppm. |
| 8(1) | Major Isomer: 1.90(3H, s); 2.34(3H, s); 3.65(3H, s); 3.79(3H, s); 4.91(2H, s); 5.13(2H, s); 7.10–7.35(7H, m); 7.48–7.59(1H, m); 7.58(1H, s)ppm.<br>Minor Isomer: 1.90(3H, s); 2.34(3H, s); 3.69(3H, s); 3.83(3H, s); 4.91(2H, s); 5.1.3(2H, s); 7.10–7.35(7H, m); 7.48–7.59(1H, m); 7.58(1H, s)ppm. |
| 10(1) | 1.99(3H, s); 3.69(3H, s); 3.81(3H, s); 4.88(2H, s); 5.01(2H, s); 7.11–7.18(1H, m); 7.27–7.35(2H, m); 7.40–7.55(4H, m); 7.58(1H, s); 7.60–7.65(1H, m)ppm. |
| 17(1) | 1.99(3H, s); 3.68(3H, s); 3.83(3H, s); 4.89(2H, s); 5.05(2H, s); 7.00–7.19(3H, m); 7.25–7.42(4H, m); 7.45–7.50(1H, m); 7.59(1H, s)ppm. |
| 1(5) | 2.12(3H, s); 3.62(3H, s); 3.78(3H, s); 4.08(2H, s); 5.02(2H, s); 7.10–7.14(1H, m); 7.24–7.39(7H, m); 7.46–7.51(1H, m), 7.56(1H, s)ppm. |
| 10(5) | 2.00(3H, s); 3.65(3H, s); 3.80(3H, s); 4.10(2H, s); 5.00(2H, s); 7.15–7.20(1H, m); 7.25(1H, s); 7.30–7.35(3H, m); 7.35–7.50(3H, m); 7.55(1H, s)ppm. |
| 16(5) | 2.00(3H, s); 3.65(3H, s); 3.78(3H, s); 3.80(3H, s); 4.00(2H, s); 5.05(2H, s); 6.70(2H, d); 7.15–7.20(3H, m); 7.30–7.35(2H, m); 7.40–7.45(1H, m); 7.60(1H, s)ppm. |

The compounds of formula (I) can be prepared by reacting a thioester of formula (II) with a substituted hydroxylamine of formula (III) optionally in a convenient solvent such as diethyl ether or tetrahydrofuran at a temperature of 20–110° C.

Alternatively, the compounds of formula (I) can be prepared by reacting an oxime of formula (IV), wherein L is a leaving group, with a benzyl alcohol or benzyl thiol of formula (V), optionally in the presence of a base (such as sodium hydride, triethylamine, pyridine or potassium carbonate), optionally in a convenient solvent (such as N,N-dimethylformamide, tetrahydrofuran or methyl ethyl ketone) and at a temperature of 20–110° C. Examples of the L group are halogen (including chlorine, bromine or iodine), mesylate or $CH_3SO_2$.

The intermediate oxime compounds of formula (IV) can be prepared by reacting an oxime of formula (VI) with a benzyl bromide of formula (VII) optionally in the presence of a base (such as sodium hydride, triethylamine, pyridine or potassium carbonate), optionally in a convenient solvent (such as N,N-dimethylformamide, tetrahydrofuran or methyl ethyl ketone) and at a temperature of 20–110° C.

Alternatively, an intermediate oxime compound of formula (IV) can be prepared by reacting a compound of formula (VIII) with a suitable oxidising agent (such as m-chlorophenoxybenzoic acid or potassium peroxymonosulphate (sold under the Registered Trade Mark "OXONE")) in a suitable solvent (such as dichloromethane) and at a temperature in the range of 0–50° C., preferably ambient temperature. A compound of formula (VIII) can be prepared by reacting a compound of formula (VII) with a compound of formula (IV), wherein L is $CH_3S$, in the presence of a suitable base (such as sodium hydride), in a suitable solvent (such as N,N-dimethylformamide) and at a temperature in the range 0–100° C. (such as at 10° C.). A compound of formula (IV), wherein L is $CH_3S$, can be prepared by reacting a compound of formula (IV), wherein L is chlorine, with the sodium salt of methyl mercaptan (that is, $NaSCH_3$) in the presence of a suitable solvent (such as N,N-dimethylformamide) at room temperature.

In another aspect the present invention provides a process for the preparation of a compound of formula (I).

The compounds are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personatum* on peanuts and other Cercospora species on other hosts, for example, sugar beet, bananas, soya beans and rice; *Botrytis cinerea* (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and maize; Ramularia spp. on sugar beet and other hosts; post-harvest diseases particularly of fruit (e.g. *Pencillium digitatum* and *P. italicum* and *Trichoderma viride* on oranges, *Colletotrichum musae* and *Gloeosporium musarum* on bananas and *Botrytis cinereaon* grapes); other pathogens on vines, notably *Eutypa lata, Guignardia bidwellii, Phellinus igniarus, Phomopsis viticola, Pseudopezicula tracheiphila* and *Stereum hirsutum*; other pathogens on lumber, notably *Cephaloascus fragrans*, Ceratocystis spp., *Ophiostoma piceae*, Penicillium spp., *Trichoderma pseudokoningii, Trichoderma viride Trichoderma harzianum, Aspergillus niger, Leptographium lindbergi* and *Aureobasidium pullulans*; and fungal vectors of viral diseases e.g. *Polymyxa graminis* on cereals as the vector of barley yellow mosaic virus (BYMV).

Some of the compositions show a broad range of activities against fungi in vitro.

Further, some of the compositions may be active as seed dressings against pathogens including Fusarium spp., Septoria spp., Tilletia spp., (e.g. bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrol-idone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibilitylsolubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

An additional fungicidal compound may be present in the composition of the invention. By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1 H-1,2,4-triazol-1-yl-methyl)butyronitrile, (Z)-N-but-2-enyloxymethyl-2-chloro-2',6'-diethylacet-anilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-g-butyrolactone, N-(2-methoxy-5-pyridyl)-cyclo-propane carboxamide, alanycarb, aldimorph, ampropylfos, anilazine, azaconazole, BAS 490F, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprodinyl, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, 0,0-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methylthioethylideneamino-oxy-carbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furametpyr, furalaxyl, furconazole-cis, guazatine, hexaconazole, hydroxyisoxazole, hymexazole, ICIA5504, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, metconazole, methfuroxam, metiram, metiram-zinc, metsulfovax, myclobutanil, NTN0301, neoasozin, nickel dimethyldithiocarbamate, nitrothal-isopropyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quintozene, rabenazole, sodium pentachloro-phenate, streptomycin, sulphur, tebuconazole, techlofthalam, tecnazene, tetraconazole, thiabendazole, thicyofen, thifluzamide, 2-(thiocyanomethyl-thio)benzothiazole, thiophanate-methyl, thiram, timibenconazole, tolclofos-methyl, tolylfluanid, triacetate salt of 1,1'-iminodi(octamethylene)-diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The compounds of formula (I) may also be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The insecticidal compositions may also comprise another pesticidal material, for example another insecticide or acaricide, or a fungicide, or may also comprise an insecticide synergist, such as for example dodecyl imidazole, safroxan, or piperonyl butoxide.

The insecticidal compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the insecticidal compositions may be in the form of baits wherein the active ingredient is mixed with a nutrient carrier for example sucrose, yeast, malt extract, cereal or cereal products and optionally an attractant such as a pheromone or pheromone analogue.

Alternatively the insecticidal compositions may be in the form of liquid preparations to be used as dips or sprays, which are generally aqueous dispersions or emulsions of the active ingredient in the presence of one or more known wetting agents, dispersing agents or emulsifying agents (surface active agents) of the type described above for the fungicidal compositions.

The insecticidal compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2- pyrrolidone and tetrahydrofurfuryl alcohol (THFA).

The insecticidal compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000 g/ha) is particularly useful.

In use the insecticidal compositions are applied to the pests, to the locus of the pests, to the habitat of the pests, to growing plants liable to infestation by the pests, or, where there is systemic uptake by plants, to the soil surrounding plants liable to infestation, by any of the known means of applying pesticidal compositions, for example, by dusting or spraying.

The compounds of the invention may be the sole active ingredient of the insecticidal composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambda-cyhalothrin, cypermethrin, alpha cypermethrin, bifenthrin, fenpropathrin, cyfluthrin, tefluthrin, fish safe pyrethroids for example ethofenprox, natural pyrethrin, tetramethrin, s-bioallethrin, fenfluthrin, prallethrin, or 5-benzyl-3-furylmethyl-(E)-(1 R,3 S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, triazophos, methamidophos, dimethoate, phosphamidon, malathion, chloropyrifos, phosalone, fensulfothion, fonofos, phorate, phoxim, pirimiphos-methyl, fenitrothion or diazinon;

c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, or azocyclotin;

f) Macrolides such as avermectins or milbemycins, for example such as abamectin, ivermectin, and milbemycin;

g) Hormones such as pheromones;

h) Organochlorine compounds such as-benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, acaricides such as dicofol, propargite, bromopropylate, chlorobenzilate, or growth regulators such as hydramethylnon, cyromazine, methoprene, hydroprene, chlorfluazuron and diflubenzuron may also be included in the compositions.

Examples of suitable insecticide synergists for use in the compositions include piperonyl butoxide, sesamex, and dodecyl imidazole.

Suitable herbicides, fungicides and plant-growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compounds of formula I and insecticidal compositions comprising them have shown themselves active against a variety of insect and other invertebrate pests. They are particularly useful in controlling sucking pests such as aphids and mites. Compounds of the present invention are also generally characterised by a relatively broad spectrum of activity which may include Lepidoptera and Coleoptera in addition to public health pests such as flies and cockroaches.

They may also be active against organophosphate, pyrethroid or cyclodiene (for example lindane or dieldrin) resistant strains of public and animal health pests. They may be effective in combating both susceptible and resistant strains of the pests in their adult and immature stages of growth, and may be applied to the infested host animal by topical, oral or parenteral administration.

The following Examples illustrate the invention.

EXAMPLE 1

This Example illustrates the preparation of (E),(E)-methyl 2-[2-(benzyloxyacetoximinomethyl)phenyl]-3-methoxypropenoate (Compound No. 1 in Table 1).

Benzyl acetate (4.19 g, 27.9 mmol) and 2,4-bis(4-methoxyphenyl)-1,3-dithia-2,4-diphosphetane-2,4-disulphide (6.15 g, 14.0 mmol) (Lawesson's Reagent) in toluene (25 ml) were heated at reflux for 7 days. After cooling to room temperature the solution was purified by column chromatography (silica eluted with hexane) to give benzylthioacetate (2.32 g, 50%) as an orange oil.

(E)-methyl 2-[phthalimidooxymethylphenyl]-3-methoxypropenoate (1.11 g, 3.02 mmol) (prepared as described in Example 4 of EP 0463488) was suspended in methanol (25 ml) at room temperature and hydrazine hydrate (0.151 g, 3.02 mmol) was added. The resulting solution was stirred for 3 hours. The white precipitate which formed was filtered off and the solvent removed to give a white semi-solid. This was diluted with diethyl ether, and the white solid filtered off to give (E)-methyl 2-[2-aminooxymethylphenyl]-3-methoxypropenoate (93%) as a yellow oil which was used immediately in the next stage without further purification.

(E)-Methyl 2-[2-aminooxymethylphenyl]-3-methoxypropenoate (prepared as above) was dissolved in tetrahydrofuran (20 ml) and benzylthioacetate (0.502 g, 3.02 mmol) was added dropwise. The resulting solution was stirred at 50° C. for 12 hours. After cooling to room temperature the solvent was removed to give a yellow gum. This was purified by column chromatography (silica eluted with hexane : diethyl ether 1:1) to give the title compound (0.382 g, 34%) as a clear gum.

EXAMPLE 2

This Example illustrates the preparation of (E),(E) and (Z), (E)-methyl 2-[2-(4-methylbenzyloxyacetoximinomethyl)phenyl-3-methoxypropenoate (Compound No. 7 in Table 1).

Stage 1

A solution of (E)-methyl 2-[2-bromomethylphenyl]-3-methoxypropenoate (2.71 g) in N,N-dimethylformamide (7 ml) was added dropwise to the sodium salt of 3-thiomethoxyacetaldoxime [prepared from 3-thiomethoxyacetaldoxime (1.00 g) and sodium hydride (0.290 g)] in N,N-dimethylformamide (7 ml) at 20° C. The mixture was then stirred overnight, poured into water and extracted with diethyl ether. The ethereal extracts were washed with water, dried and the solvent removed to give a crude gum which was purified by high performance liquid chromatography using silica-gel eluted with ethyl acetate:hexane 1:1, to give (E),(E)- and (Z),(E)-methyl[2-(2-thiomethoxyacetoximinomethyl)phenyl]-3-methoxypropenoate (1.47 g, 50%) as a yellow gum.

Stage 2

To a solution of (E),(E) and (Z),(E)-methyl 2-[2-(thiomethoxyacetoximinomethyl)phenyl]-3-methoxypropenoate (2.50 g) in methanol (75 ml) was added potassium peroxymonosulphate (sold under the Registered Trade Mark "OXONE") (9.95 g) in water (35 ml). The mixture was stirred overnight, poured into water and extracted with ethyl acetate. The combined organic phases were washed with water, dried and the solvent removed to give a gum which was purified by flash column chromatography, using silica-gel eluted with diethyl ether:hexane 1:2, to give (E),(E) and (Z),(E)-methyl 2-[2-(methylsulphonylacetoximinomethyl)phenyl]-3-methoxypropenoate (0.802 g, 29%) as a clear gum.

Stage 3

A solution of (E),(E) and (Z),(E)-methyl 2-[2-(methylsulphonylacetoximinomethyl)phenyl]-3-methoxypropenoate (0.220 g) in N,N-dimethylformamide (5 ml) was added dropwise to the sodium salt of p-methylbenzyl alcohol [prepared from p-methylbenzyl alcohol (0.158 g) and sodium hydride (0.052 g)]in N,N-dimethylformamide (5 ml) at 20° C. The mixture was stirred for three hours and then poured into water and extracted with ethyl acetate. The combined organic phases were washed with water, dried and the solvent removed to give a gum which was purified by flash column chromatography, using silica-gel eluted with hexane:ether 1:1, to give (E),(E) and (Z),(E)-methyl 2-[2-(4-methylbenzyloxyacetoximinomethyl)-phenyl]-3-methoxypropenoate (0.115 g, 47%) as a clear gum.

EXAMPLE 3

This Example illustrates the preparation of (E),(E)-methyl 2-[2-(3-trifluoromethyl)benzylthiolacetoximinomethyl)phenyl]-3-methoxypropenoate (Compound No. 10 in Table 5).

A solution of (E),(E) and (Z),(E)-methyl 2-[2-(methylsulphonylacetoximinomethyl)phenyl]-3-methoxypropenoate (0.300 g) in N,N-dimethylformamide (7 ml) was added dropwise to the sodium salt of 3-trifluoromethylbenzyl mercaptan [prepared from 3-trifluromethylbenzyl mercaptan (0.203 g) and sodium hydride (0.042 g, a 60% dispersion in oil) in N,N-dimethylformamide (8 ml) at 10° C. The mixture was stirred for 5 hours, allowed to stand overnight and then poured into water and extracted with diethyl ether. The combined organic phases were washed with water, dried and the solvent removed to give a gum which was purified by flash column chromatography, using silica-gel eluted with hexane:ether 2:1, to give the title compound (0.224 g, 58%) as a gum.

EXAMPLE 4

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous DISPERSOL T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. TWEEN 20 was added to give a final concentration of 0.05% when the sprays were applied to cereals.

For most of the tests the compounds were applied to the soil (roots) or to the foliage (by spraying) one or two days before the plant was inoculated with the disease. Exceptions were the test on Erysiphe graminis in which the plants were inoculated 24 hours before treatment and the test on Puccinia recondita in which the plants were inoculated 48 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

| | |
|---|---|
| 0 = 0% disease present | 20 and 24 = 10.1 – 20% disease present |
| 1 = 0.1 – 1% disease present | 30 = 20.1 – 30% disease present |
| 3 = 1.1 – 3% disease present | 60 = 30.1 – 60% disease present |
| 5 = 3.1 – 5% disease present | 90 and 94 = 60.1 – 100% disease present |
| 10 = 5.1 – 10% disease present | |

Each assessment was then expressed as a percentage of the level of disease present on the untreated control plants. This calculated value is referred to as a POCO (Percentage of Control) value. An example of a typical calculation is as follows:

Disease level on untreated control = 90

Disease level on treated plant = 30

-continued $$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table II.

TABLE II

| Compound No (Table No) | Pr | Egt | Sn | Po | Tc | Vi | Pv | Pil |
|---|---|---|---|---|---|---|---|---|
| 1(1) | 0 | 0 | 0 | 0 | 0 | 0 | — | 0 |
| 4(1) | 0 | — | 0 | — | 0 | 0 | 0 | 0 |
| 7(1) | 0 | 0 | 0 | 0 | 0 | 0 | 0 | 0 |
| 8(1) | 0 | 0 | 0 | 0 | 0 | 0 | 0 | 0 |
| 10(1) | 0$^b$ | 3$^a$ | 0$^a$ | — | — | — | — | — |
| 1(5) | 60 | 90 | 0 | 0 | 90 | 0 | 0 | 0 |

Pr = *Puccinia recondita*
Egt = *Erysiphe graminis tritici*
Sn = *Septoria nodorum*
Po = *Pyricularia oryzae*
Tc = *Thanatephorus cucumeris*
Vi = *Venturia inaequalis*
Pv = *Plasmopara viticola*
Pil = *Phytophthera infestans*
$^a$ = 10 ppm foliar application only
$^b$ = 5 ppm foliar application only
— = no result

EXAMPLE 5

The activity of the compounds of formula (I) was determined using a variety of pests. The pests were treated with a liquid composition containing 250 parts per million (ppm) by weight of the compound except in the case of *Meloidogyne incognita*, which was treated with a liquid composition containing 6.25 ppm by weight of the compound in an in vitro test. The compositions were made by dissolving the compound in acetone and ethanol (50:50) mixture and diluting the solutions with water containing 0.1%by weight of a wetting agent sold under the trade name "SYNPERONIC" NP8 (further diluting to 6.25 ppm in the case of *Meloidogyne incognita*) until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment with the exception of *Musca domestica*, for which an additional initial knockdown assessment was made.

The results of the tests are presented in Table III for each of the compounds. The results indicate a grading of mortality (or knockdown in the case of *Musca domestica*), designated as A, B or C wherein A indicates 80–100% mortality, B indicates 40–79% mortality and C indicates 0–39% mortality. The pest species is designated by a letter code.

Information regarding the pest species, the support medium or food, and the type and duration of the test is given in Table IV.

TABLE III

| Compound No (Table No) | Tu | Mp | Md initial knockdown/kill | Hv | Se | Db | Mi |
|---|---|---|---|---|---|---|---|
| 1(1) | A | A | A/A | C | C | A | C |

TABLE IV

| CODE LETTERS (TABLE 18) | TERST SPECIES | SUPPORT MEDIUM/ FOOD | TYPE OF TEST | DURATION (DAYS) |
|---|---|---|---|---|
| Tu | *Tetranychus urticae* (spider mite) | French bean leaf | Contact | 3 |
| Mp | *Myzus persicae* (aphid) | Chinese Cabbage leaf | Contact | 3 |
| Md | *Musca domestica* (housefly - adult) | Cotton wool/ sugar | Contact Knockdown | 2 15 min |
| Hv | *Heliothis virescens* (tobacco budworm) | Soya leaf | Residual | 5 |
| Se | *Spodoptera exigua* (lesser armyworm - larva) | Cotton leaf | Residual | 5 |
| Db | *Diabrotica balteata* (cucumber beetle - larva) | Filter paper/ maize seed | Residual | 2 |
| Mi | *Meloidogyne incognita* (rootknot nematode - larva) | in vitro | Contact | 2 |

"Contact" test indicates that both pests and medium were treated, "Residual" indicates that the medium was treated before infestation with the pests and "in vitro" indicates that the pest was suspended in an aqueous medium containing the treatment.

CHEMICAL FORMULAE (in description)

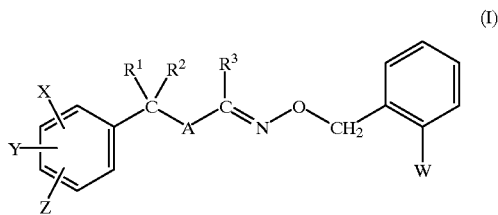

(I)

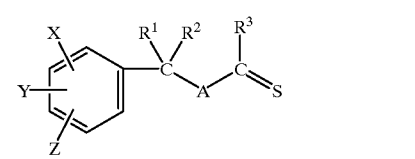

(II)

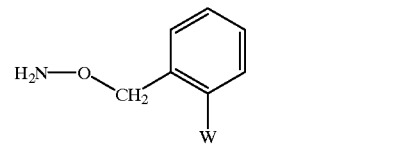

(III)

-continued

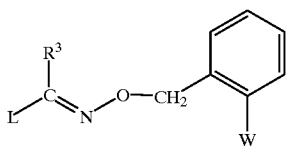
(IV)

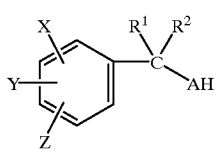
(V)

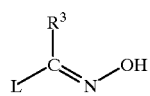
(IV)

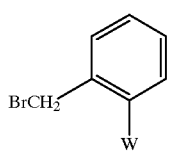
(VII)

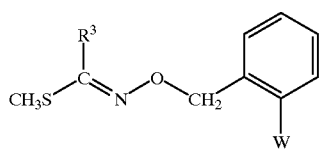
(VIII)

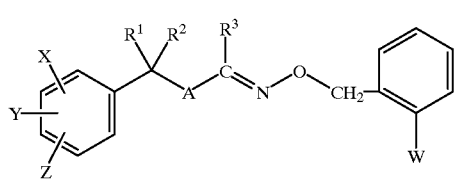

We claim:

1. A compound having the formula (I):

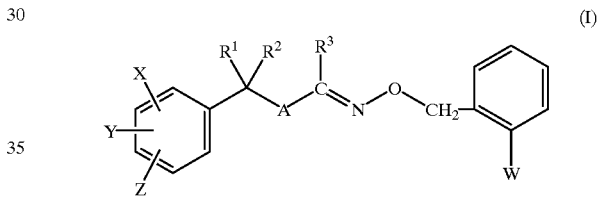
(I)

wherein $R^1$ and $R^2$ are independently hydrogen, $C_{1-4}$ alkyl, $C_{1-4}$ haloalkyl, $C_{2-4}$ alkenyl, $C_{2-4}$ alkynyl, $C_{3-6}$ cycloalkyl, aryl or aryl($C_{1-4}$)alkyl; $R^3$ is hydrogen, $C_{1-4}$ alkyl, $C_{1-4}$ haloalkyl or $C_{3-6}$ cycloalkyl; A is oxygen; W is $CH_3O.CH=CCO_2CH_3$ and stereoisomers thereof; X, Y and Z are independently hydrogen, halogen, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, optionally substituted methylenedioxy, optionally substituted aryl, optionally substituted heteroaryl, optionally substituted aryloxy, optionally substituted heteroaryloxy, optionally substituted aryl($C_{1-4}$)alkyl in which the alkyl moiety is optionally substituted with hydroxy, optionally substituted heteroaryl(-$C_{1-4}$)alkyl, optionally substituted aryl($C_{2-4}$)alkenyl, optionally substituted heteroaryl($C_{2-4}$) alkenyl, optionally substituted aryl($C_{1-4}$)alkoxy, optionally substituted heteroaryl($C_{1-4}$)alkoxy, optionally substituted aryloxy($C_{1-4}$)alkyl, optionally substituted heteroaryloxy ($C_{1-4}$)alkyl, acyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R"; heteroaryl rings are selected from the group comprising pyridinyl, pyrimidinyl, pyridazinyl, pyrazinyl, triazinyl, furyl, thienyl, pyrrolyl, pyrazolyl, imidazolyl, triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothiophenyl and benzimidazolinyl; heteroaryl rings of any of the foregoing substituents are optionally substituted by one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R"; R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; when R' and R" are in CONR'R" they can together form a 5- or 6-membered heterocyclic ring; or two substituents, when they are in adjacent positions on an aryl or heteroaryl ring may join to form a fused aliphatic ring.

2. A compound having the formula (I):

(I)

wherein $R^1$ and $R^2$ are independently hydrogen, $C_{1-4}$ alkyl, $C_{1-4}$ haloalkyl, $C_{2-4}$ alkenyl, $C_{2-4}$ alkynyl, $C_{3-6}$ cycloalkyl, aryl or aryl($C_{1-4}$)alkyl; $R^3$ is hydrogen, $C_{1-4}$ alkyl, $C_{1-4}$ haloalkyl or $C_{3-6}$ cycloalkyl; A is oxygen; W is $CH_3O.CH=CCO_2CH_3$ and stereoisomers thereof; X, Y and Z are independently hydrogen, halogen, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, optionally substituted methylenedioxy, optionally substituted aryl, optionally substituted heteroaryl, optionally substituted aryloxy, optionally substituted heteroaryloxy, optionally substituted aryl($C_{1-4}$)alkyl in which the alkyl moiety is optionally substituted with hydroxy, optionally substituted heteroaryl($C_{1-4}$)alkyl, optionally substituted aryl ($C_{2-4}$)alkenyl, optionally substituted heteroaryl($C_{2-4}$) alkenyl, optionally substituted aryl($C_{1-4}$)alkoxy, optionally substituted heteroaryl($C_{1-4}$)alkoxy, optionally substituted aryloxy($C_{1-4}$)alkyl, optionally substituted heteroaryloxy ($C_{1-4}$)alkyl, acyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R"; heteroaryl rings are selected from the group comprising pyridinyl and pyrimidinyl; heteroaryl rings of any of the foregoing substituents are optionally substituted by one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)

alkoxy, $C_{1-4}$ alkylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R"; R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups-being optionally substituted with halogen, $C_{1-4}$ alkyl or $C_{1-4}$ alkoxy; when R' and R" are in CONR'R" they can together form a 5- or 6-membered heterocyclic ring; or two substituents, when they are in adjacent positions on the aryl or heteroaryl ring can join to form a fused alphatic ring.

3. A compound as claimed in claim 1, wherein $R^3$ is methyl.

4. A compound as claimed in claim 1, wherein $R^1$ and $R^2$ are, independently, hydrogen or methyl.

5. A compound as claimed in claim 1 wherein X, Y and Z are, independently, hydrogen, halogen, hydroxy, mercapto, $C_{1-4}$ alkyl, $C_{2-4}$ alkenyl, $C_{2-4}$ alkynyl, halo($C_{1-4}$) alkyl, $C_{1-4}$ alkoxy, $C_{2-4}$ alkenyloxy, $C_{2-4}$ alkynyloxy, halo ($C_{1-4}$)alkoxy, $C_{1-4}$ alkylthio, hydroxy($C_{1-4}$)alkyl, $C_{1-4}$ alkoxy,($C_{1-4}$)alkyl, $C_{3-6}$ cycloalkyl, $C_{3-6}$ cycloalkyl ($C_{1-4}$) alkyl, acyloxy, cyano, thiocyanato, nitro, —NR'R", —NHCOR', —CONR'R", —COOR' or —COR', wherein R' and R" are, independently, hydrogen, $C_{1-4}$ alkyl or $C_{3-6}$ cycloalkyl.

6. A compound as claimed in claim 1 wherein X, Y and Z are, independently, hydrogen, halogen, $C_{1-4}$ alkyl, cyano, $C_{1-4}$ alkoxy, halo($C_{1-4}$)alkyl, halo($C_{1-4}$)alkoxy or nitro.

7. A fungicidal composition comprising a fungicidally effective amount of a compound according to claim 1 and a fungicidally acceptable carrier or diluent therefor.

8. A method of combating fungi which comprises applying to plants, to the seeds of plants or to the locus of the plants or seeds, a compound according to claim 1.

9. An insecticidal composition comprising an insecticidally or acaricidally effective amount of a compound according claim 1 and an insecticidally or acaricidally acceptable carrier or diluent therefor.

10. A method of combating insect or acarine pests which comprises applying to the locus of the pest, an insecticidally or acaricidally effective amount of a compound according to claim 1.

11. A process for preparing a compound of formula (I) as claimed in claim 1, the process comprising either:

(a) reacting a thioester of formula (II):

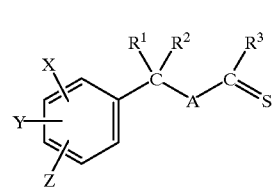

(II)

with a hydroxylamine of formula (III):

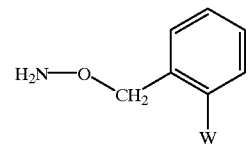

(III)

or (b) racting an oxime of formula (IV):

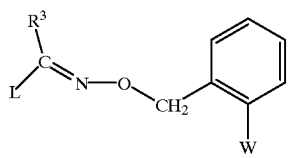

(IV)

wherein L is a leaving group, with a benzyl alcohol or benzyl thiol of formula (V):

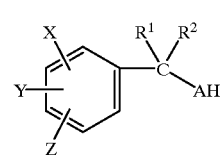

(V)

* * * * *